United States Patent
Kudo et al.

(10) Patent No.: US 7,132,585 B2
(45) Date of Patent: Nov. 7, 2006

(54) ABSORBENT ARTICLE WITH LIQUID ACQUISITION LAYER

(75) Inventors: Jun Kudo, Kagawa (JP); Masahiro Kashiwagi, Kagawa (JP); Masataka Kinoshita, Kagawa (JP); Kenichiro Kuroda, Kagawa (JP); Takuya Miyama, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 11/059,058

(22) Filed: Feb. 16, 2005

(65) Prior Publication Data

US 2005/0148970 A1 Jul. 7, 2005

Related U.S. Application Data

(63) Continuation of application No. pct/jp03/15389, filed on Dec. 2, 2003.

(30) Foreign Application Priority Data

Dec. 5, 2002 (JP) ............................. 2002-354186

(51) Int. Cl.
*A61F 13/15* (2006.01)
(52) U.S. Cl. ...................... 604/380; 604/369
(58) Field of Classification Search ............... 604/380, 604/378, 369, 384, 385.101, 383
See application file for complete search history.

(56) References Cited

U.S. PATENT DOCUMENTS

| 810,121 | A | * | 1/1906 | Green | 604/378 |
|---|---|---|---|---|---|
| 810,128 | A | * | 1/1906 | Green | 604/378 |
| 2,896,618 | A | * | 7/1959 | Schaefer | 602/47 |
| 3,375,827 | A | * | 4/1968 | Bletzinger et al. | 604/380 |
| 3,459,618 | A | * | 8/1969 | Egler | 156/219 |
| 3,965,906 | A | * | 6/1976 | Karami | 604/366 |
| 4,072,150 | A | * | 2/1978 | Glassman | 604/389 |
| 4,389,211 | A | * | 6/1983 | Lenaghan | 604/383 |
| 4,988,344 | A | * | 1/1991 | Reising et al. | 604/368 |
| 5,062,418 | A | * | 11/1991 | Dyer et al. | 602/45 |
| 5,180,620 | A | * | 1/1993 | Mende | 428/138 |
| 5,268,213 | A | * | 12/1993 | Murakami et al. | 428/163 |
| 5,328,450 | A | * | 7/1994 | Smith et al. | 602/59 |
| 5,368,909 | A | * | 11/1994 | Langdon et al. | 428/137 |
| H1511 | H | * | 12/1995 | Chappell et al. | 604/383 |
| 5,505,720 | A | * | 4/1996 | Walters et al. | 604/378 |
| 5,591,150 | A | * | 1/1997 | Olsen et al. | 604/385.23 |
| 5,603,707 | A | * | 2/1997 | Trombetta et al. | 604/383 |
| 5,614,283 | A | * | 3/1997 | Potnis et al. | 428/131 |
| 5,674,341 | A | * | 10/1997 | Ng | 156/234 |

(Continued)

FOREIGN PATENT DOCUMENTS

EP 1090615 A1 * 4/2001

(Continued)

*Primary Examiner*—Tatyana Zalukaeva
*Assistant Examiner*—Paula L. Craig
(74) *Attorney, Agent, or Firm*—Darby & Darby

(57) ABSTRACT

Disclosed is an absorbent article having a liquid acquisition layer between a topsheet and a liquid absorbent layer. The liquid acquisition layer is an absorbent sheet that is three-dimensionally deformed to include: longitudinal ribs projecting toward the topsheet and extending parallel with each other in a longitudinal direction of the article; and transverse ribs projecting toward the topsheet and extending in a transverse direction of the article. The transverse ribs are arranged at intervals in the longitudinal direction and connect adjacent longitudinal ribs, thereby providing a plurality of recesses surrounded by the longitudinal ribs and the transverse ribs. At least the longitudinal ribs are in contact with an overlying component, whereas bottoms of the recesses are in contact with the liquid absorbent layer.

7 Claims, 9 Drawing Sheets

U.S. PATENT DOCUMENTS

| | | | | |
|---|---|---|---|---|
| 5,902,260 | A * | 5/1999 | Gilman et al. | 602/57 |
| 5,902,757 | A * | 5/1999 | Stern et al. | 442/324 |
| 5,925,026 | A * | 7/1999 | Arteman et al. | 604/383 |
| 5,941,863 | A * | 8/1999 | Guidotti et al. | 604/378 |
| 6,090,994 | A * | 7/2000 | Chen | 604/378 |
| 6,241,714 | B1 * | 6/2001 | Raidel et al. | 604/378 |
| 6,245,961 | B1 * | 6/2001 | Roxendal et al. | 604/367 |
| 6,372,954 | B1 * | 4/2002 | Johnston et al. | 604/378 |
| 6,413,248 | B1 * | 7/2002 | Mizutani | 604/385.17 |
| 6,436,082 | B1 * | 8/2002 | Mizutani et al. | 604/385.101 |
| 6,503,598 | B1 * | 1/2003 | Goda et al. | 428/137 |
| 6,569,137 | B1 * | 5/2003 | Suzuki et al. | 604/385.01 |
| 7,005,558 | B1 * | 2/2006 | Johansson et al. | 604/383 |
| 7,015,370 | B1 * | 3/2006 | Watanabe et al. | 604/378 |
| 2001/0020157 | A1 * | 9/2001 | Mizutani et al. | 604/385.04 |
| 2001/0037103 | A1 * | 11/2001 | Onishi | 604/385.19 |
| 2002/0151861 | A1 * | 10/2002 | Klemp et al. | 604/385.19 |
| 2002/0173759 | A1 * | 11/2002 | D'Acchioli et al. | 604/347 |
| 2003/0060792 | A1 * | 3/2003 | Harriz et al. | 604/385.04 |
| 2003/0088222 | A1 * | 5/2003 | Yoshimasa et al. | 604/380 |
| 2003/0211801 | A1 * | 11/2003 | Putnam et al. | 442/387 |

FOREIGN PATENT DOCUMENTS

| | | |
|---|---|---|
| JP | 55-94251 | 7/1980 |
| JP | 06-038998 | 2/1994 |
| JP | 2000-140015 | 5/2000 |
| JP | 2001-095845 | 4/2001 |

* cited by examiner

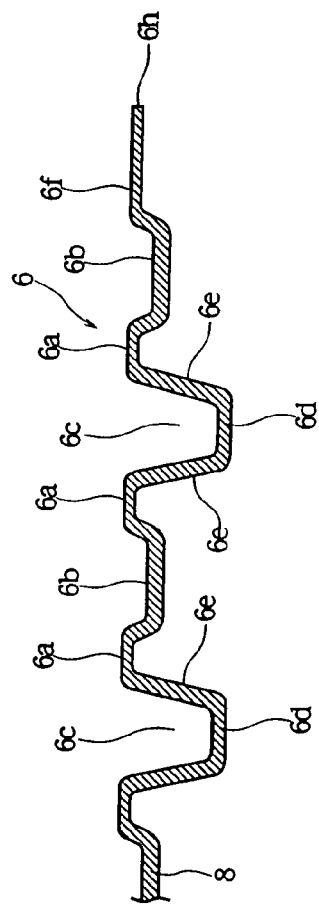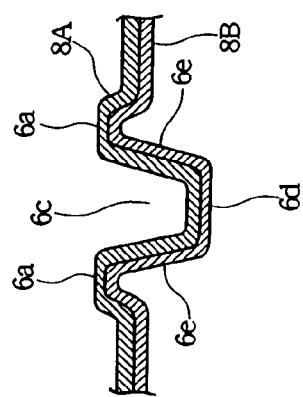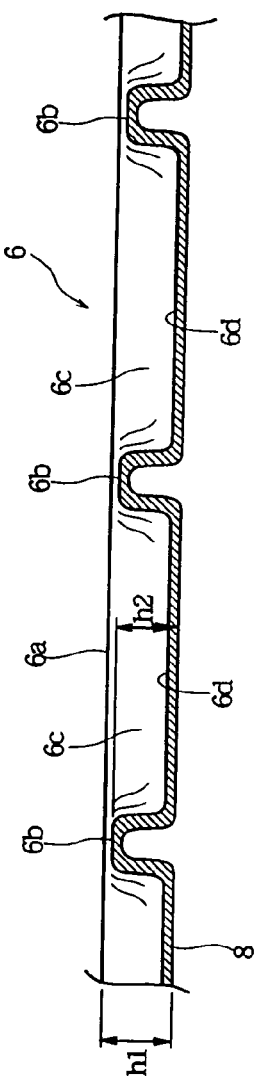

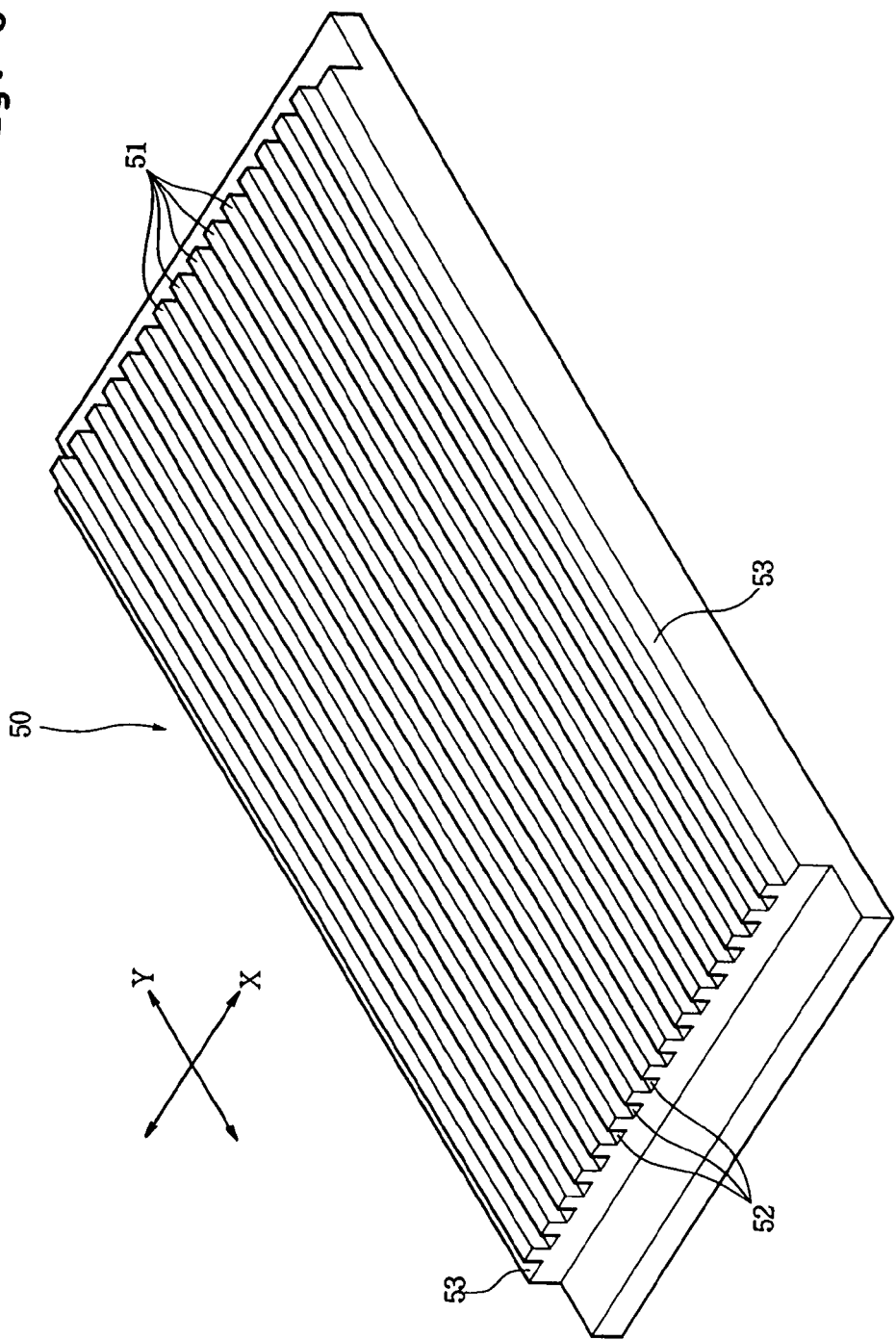

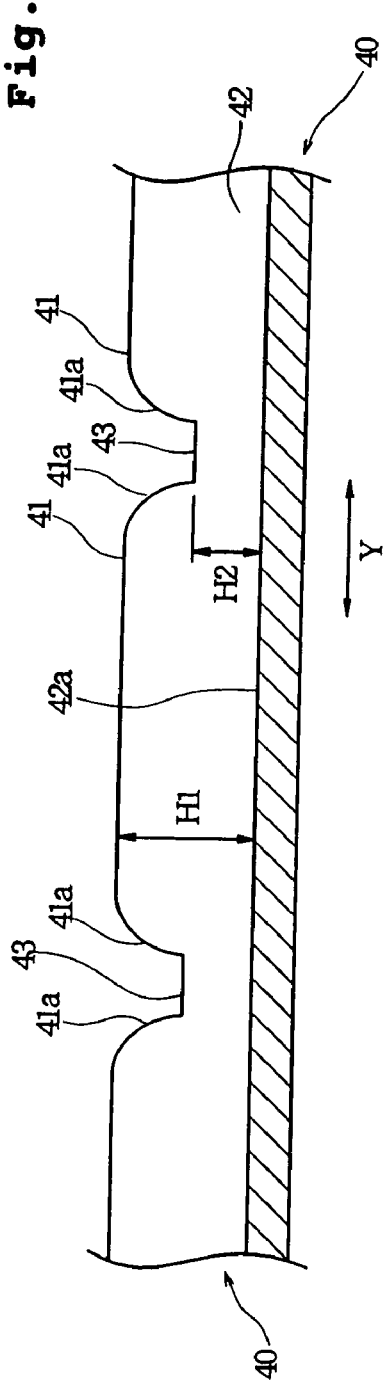
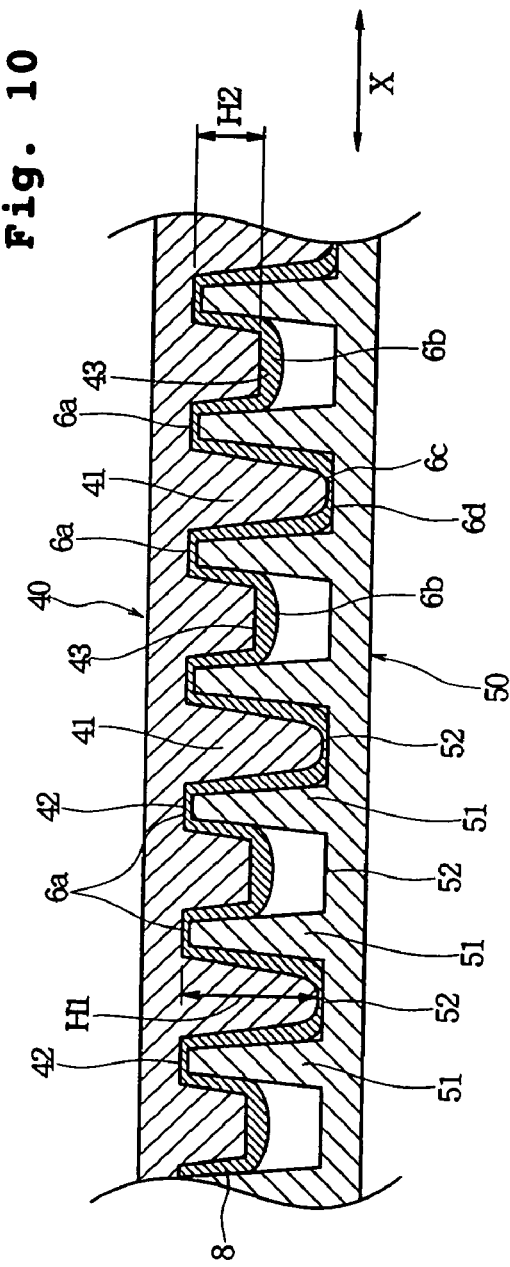

ABSORBENT ARTICLE WITH LIQUID ACQUISITION LAYER

CROSS-REFERENCE TO RELATED APPLICATIONS

This application is a continuation of International Patent Application No. PCT/JP2003/15389, filed on Dec. 2, 2003, which claims priority from Japanese Patent Application No. 2002-354186, filed on Dec. 5, 2002.

BACKGROUND OF THE INVENTION

1. Field of the Invention

The present invention relates to an absorbent article suitable for absorbing menstrual blood and so on discharged from a woman's genital organ, more particularly, relates to an absorbent article having a liquid acquisition layer between a topsheet and a liquid absorbent layer so as to absorb liquid and introduce it into the liquid absorbent layer.

2. Description of the Related Art

Absorbent articles intended to absorb menstrual blood discharged from a woman's genital organ are typically constructed to include a liquid-permeable topsheet appearing on its skin surface, a liquid-impermeable backsheet appearing on its garment surface and a liquid absorbent layer disposed between the topsheet and the backsheet, and generally, they are worn with the backsheet adhered to an inner side of a groin piece of an undergarment through a pressure-sensitive adhesive layer.

In such an absorbent article, if a large amount of menstrual blood is given to the topsheet at a time, menstrual blood remains in the topsheet for a long time, making a wearer uncomfortable due to wet feeling in the crotch. Therefore, there have been known absorbent articles devised to diffuse or retain liquid beneath the topsheet when a large amount of liquid is given thereto at a time.

Japanese Unexamined Patent Publication No. 6-38998 (Patent Publication 1) discloses a sanitary napkin in which a liquid transferring band is disposed between the topsheet and the liquid absorbent layer.

The liquid transferring band is nonwoven fabric formed with a screen pattern of a large number of recesses. The screen pattern is composed of an embossed pattern, in which high fiber density portions are formed by compressing a given thickness of nonwoven fabric from one side, and an embossed pattern, in which membrane portions are formed by compressing the nonwoven fabric from both sides, wherein both embossed patterns are arranged in a longitudinal (lengthwise) direction of the sanitary napkin. In the liquid transferring band, movement of menstrual blood having passed through the topsheet is restricted by the membrane portions so that the menstrual blood can be diverted and introduced into the high fiber density portions, thereby diffusing menstrual blood in the longitudinal direction so as to prevent liquid from being left in the topsheet.

On the other hand, Japanese Unexamined Patent Publication No. 2000-140015 (Patent Publication 2) discloses a disposable diaper in which a liquid permeable sheet is disposed between the topsheet and the liquid absorbent layer.

This liquid permeable sheet is nonwoven fabric or paper that is three-dimensionally deformed to have a large number of recesses defined by projections extending in a net-like pattern. This disposable diaper is intended to prevent liquid from flowing along a surface of the diaper by temporarily retaining liquid in the recesses formed in the liquid permeable sheet even when a large amount of liquid is applied at a time.

In the liquid transferring belt disclosed in Patent Publication 1, liquid having passed through the topsheet can be diffused in the longitudinal direction, but because the liquid transferring belt itself is inferior in both liquid retention ability and liquid permeability, the liquid transferring belt will be immediately saturated if a large amount of menstrual blood is applied thereto, easily causing the problem of liquid residue. In detail, the liquid transferring belt is meltblown nonwoven fabric formed with an embossed pattern, wherein since the meltblown nonwoven fabric remains relatively flat even after embossing, a large amount of liquid locally applied thereto cannot be retained. Furthermore, since recesses forming the embossed pattern in the nonwoven fabric are of an extremely small space volume, little liquid will be retained in the recesses. Rather, the meltblown nonwoven fabric is inferior in liquid permeability not only because such meltblown nonwoven fabric itself is of a high density but also because the membrane portions block liquid permeation.

On the other hand, the liquid permeable sheet disclosed in Patent Publication 2 is intended to retain urine in triangular recesses so as to prevent diffusion along the sheet. However, since liquid diffusion is inhibited by the net-like projections, the recesses will be saturated with urine in a short period of time. Accordingly, if the liquid permeable sheet is adopted for sanitary napkins, menstrual blood that is thicker than urine will be easily left in the recesses. Moreover, Patent Publication 2 teaches that the liquid permeable sheet is preferably formed of paper, but if such a liquid permeable sheet formed of paper is adopted for sanitary napkins, the recesses will be immediately crushed by a pressure applied from the wearer's crotch and the liquid permeable sheet will be easily broken when an offset force acts on the sanitary napkin.

SUMMARY OF THE INVENTION

The present invention has been worked out in view of the shortcomings in the prior art set forth above. It is therefore an object of the present invention to provide an absorbent article, in which a large amount of liquid applied thereto can be temporarily retained and smoothly transferred into a liquid absorbent layer, reducing the amount of liquid residue in a topsheet.

According to the present invention, there is provided an absorbent article comprising: a liquid-permeable topsheet appearing on a skin surface; a backsheet appearing on a garment surface; and a liquid absorbent layer disposed between the topsheet and the backsheet, wherein a liquid acquisition layer is disposed on a surface of the liquid absorbent layer that is directed to the topsheet, the liquid acquisition layer being kept in a three-dimensionally deformed state, wherein the liquid acquisition layer is an absorbent sheet that is three-dimensionally deformed to include: longitudinal ribs projecting toward the topsheet and extending parallel with each other in a longitudinal direction of the article; and transverse ribs projecting toward the topsheet and extending in a transverse direction of the article, the transverse ribs being arranged at intervals in the longitudinal direction and connecting adjacent longitudinal ribs, thereby providing a plurality of recesses surrounded by the longitudinal ribs and the transverse ribs, wherein at least the longitudinal ribs are in contact with an overlying component, whereas bottoms of the recesses are in contact with the liquid absorbent layer.

In the absorbent article of the present invention, menstrual blood having passed through the topsheet can be temporarily retained in the recesses formed in the liquid acquisition layer, wherein since the liquid acquisition layer is formed by deforming an absorbent sheet three-dimensionally to increase its sheet thickness, the space volume of the individual recessed can be made large, as compared with the case where an embossed pattern is formed in nonwoven fabric without increasing its sheet thickness, so that a large amount of menstrual blood can be temporarily retained in the recesses. In addition, since the bottoms of the recesses obtained by deforming the absorbent sheet are in contact with the liquid absorbent layer, menstrual blood in the recesses can be transferred into the liquid absorbent layer immediately after permeation through the absorbent sheet, preventing menstrual blood from being retained in the recesses for a long period of time. Moreover, since the longitudinal ribs are extended along the longitudinal direction of the article and in contact with an overlying component such as topsheet or liquid permeable layer, liquid retained in the recesses can be easily led along the longitudinal direction, inhibiting diffusion in the transverse direction. Therefore, menstrual blood easily permeates through the liquid absorbent layer without causing leakage in the transverse direction.

The liquid acquisition layer of the present invention may be constructed such that a height from the bottoms of the recesses to tops of the transverse ribs is smaller than a height from the bottoms of the recesses to tops of the longitudinal ribs.

With this construction, even if a large amount of menstrual blood is given to the recesses at a time, menstrual blood can move along recesses arranged in the longitudinal direction beyond the lower transverse ribs, so that diffusion in the transverse direction (i.e., diffusion beyond the longitudinal ribs) can be effectively prevented.

To this end, it is preferred that the individual recesses are elongated to be longer in the longitudinal direction than in the transverse direction.

In the present invention, it is also preferred that each recess has a space volume of 8 to 80 $mm^3$.

With the space volume in the above-mentioned range, a sufficient amount of menstrual blood can be retained in the recesses until menstrual blood being thick body fluid passes through the liquid acquisition layer. Therefore, even if a large amount of menstrual blood is applied in a short period of time, menstrual blood will hardly flow over the recesses, preventing menstrual blood from returning to the topsheet and diffusing in the transverse direction.

In the present invention, the liquid acquisition layer may have low-density portions where fiber-to-fiber distance is increased by concentration of tensile stress when the absorbent sheet is three-dimensionally deformed.

With the fiber density being partially lowered in the liquid acquisition layer, menstrual blood temporarily retained in the recesses can be immediately transferred into the liquid absorbent layer.

In the present invention, the liquid acquisition layer may also have flat portions that are of a width greater than that of the longitudinal ribs and extended continuously in the longitudinal direction.

The flat portions refer to regions that are not affected by tensile force or compressive force during three-dimensional shaping, so that the strength is not decreased. In addition, since the fiber density remains unchanged from that of the original sheet stock, the density becomes lower than that in the longitudinal ribs and so on. During assembly of the absorbent article, therefore, the liquid acquisition layer may be supplied to the assembly process with the flat portions being held. In addition, since the flat portions having a lower density than the longitudinal ribs and so on are extended in the longitudinal direction, they are able to function as diffusion-preventing zones for preventing menstrual blood from diffusing in the transverse direction. The flat portions may be positioned anywhere in the liquid acquisition layer, but are preferably formed in right and left sides of the liquid acquisition layer so as to be effective in functioning as the diffusion-preventing zones. Alternatively, the flat portions may be formed in front and rear ends of the liquid acquisition layer.

In the present invention, the liquid acquisition layer may be a stack of two or more absorbent sheets that are three-dimensionally deformed together. These absorbent sheets may be partially bonded together.

If the liquid acquisition layer is composed of two or more absorbent sheets, its basis weight can be increased to improve liquid absorption and retention capacity, and the strength of the longitudinal and transverse ribs can also be increased. It should be noted that the three-dimensional deformation may cause lowering of density or breakage in walls of the recesses of the liquid acquisition layer, but if the walls are of a multi-layer structure, such lowering of density or breakage will not be caused in only one location, so that the strength of the walls can be prevented from being extremely decreased. Accordingly, even when the absorbent article is wetted, the shape of recesses can be always maintained.

In the present invention, it is also preferred that when measured in the longitudinal direction, the liquid acquisition layer has a dry tensile breaking strength of at least 2.5 N/25 mm width.

In order to provide the liquid acquisition layer with such strength as well as suitable water absorbency, it is preferred that the absorbent sheet comprises cellulosic fibers and synthetic resin fibers. With such strength, the three-dimensional shape can be certainly maintained even under pressure applied from the wearer's body, so that the space volume of the recesses can be maintained for a long period of time.

BRIEF DESCRIPTION OF THE DRAWINGS

The present invention will be understood more fully from the detailed description given hereinafter and from the accompanying drawings of the preferred embodiments of the present invention, which, however, should not be taken to be limitative to the invention, but are for explanation and understanding only.

In the drawings:

FIGS. 5A and 5B are sectional views taken along line V—V of FIG. 4, wherein FIG. 5A shows a single-layer structure while FIG. 5B shows a multi-layer structure;

FIG. 6 is a sectional view taken along line VI—VI of FIG. 4;

FIG. 8 is a perspective view showing a lower mold for three-dimensionally shaping the liquid acquisition layer;

FIG. 9 is a sectional view taken along line IX—IX of FIG. 7;

FIG. 10 is a sectional view showing a state where the liquid acquisition layer is three-dimensionally shaped with the upper and lower molds;

DESCRIPTION OF THE PREFERRED EMBODIMENT

The present invention will be discussed hereinafter in detail in terms of the preferred embodiments according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

In the present invention, the absorbent article refers to a sanitary napkin whose primary object is to absorb menstrual blood discharged from the vaginal opening of a woman. It should be noted that the absorbent article has two major surfaces: of which one surface intended to be worn toward the wearer's crotch is referred to as "skin surface", while the other surface is referred to as "garment surface" regardless of whether a garment is worn outside the absorbent article or not.

As used herein, the term "longitudinal centerline" refers to a line which extends longitudinally to divide the absorbent article transversely in two. On the other hand, the term "transverse reference line" as used in the following first embodiment refers to a line which extends transversely to divide the absorbent article longitudinally in two, but should not be understood as limited to such a centerline. In the following second embodiment concerning an elongated absorbent article which is suitable for nighttime use by a woman and provided at its front portion with wings, for instance, the transverse reference line refers to a line which extends transversely to cross a longitudinal center of a portion intended to be brought into contact with the vaginal opening during wear.

Figure 1:
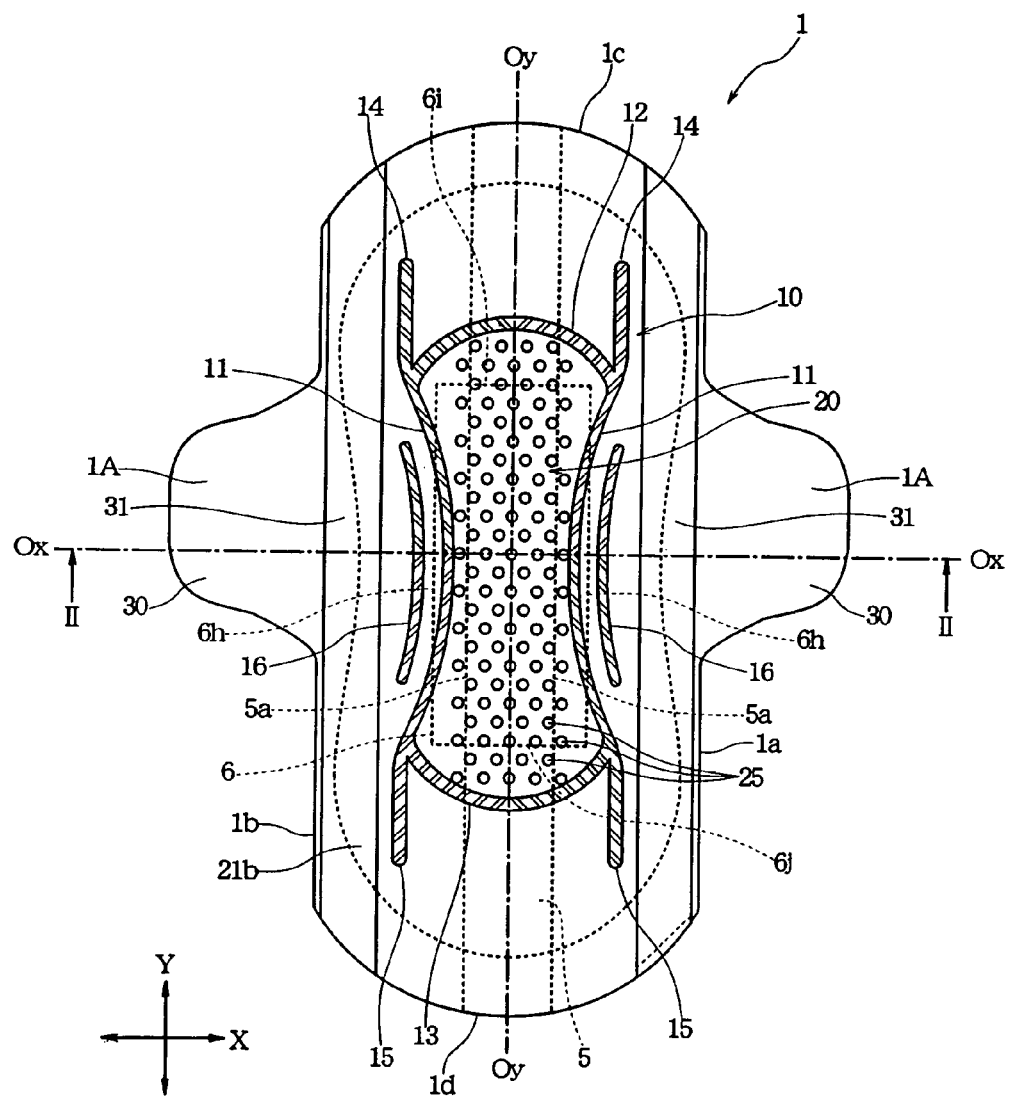
FIG. 1 is a top plan view showing a sanitary napkin as an absorbent article according to one embodiment of the present invention.
Figure 2:
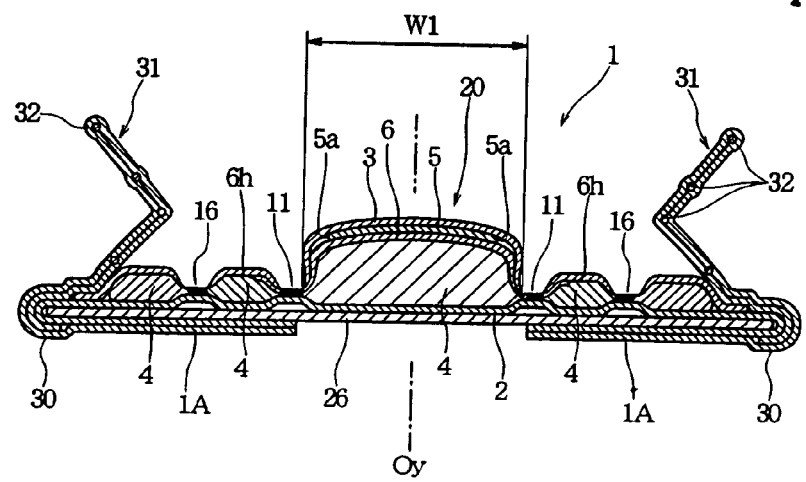
FIG. 2 is a sectional view taken along line II—II, showing a state where the sanitary napkin of FIG. 1 is attached to a groin piece of an undergarment.
Figure 3:
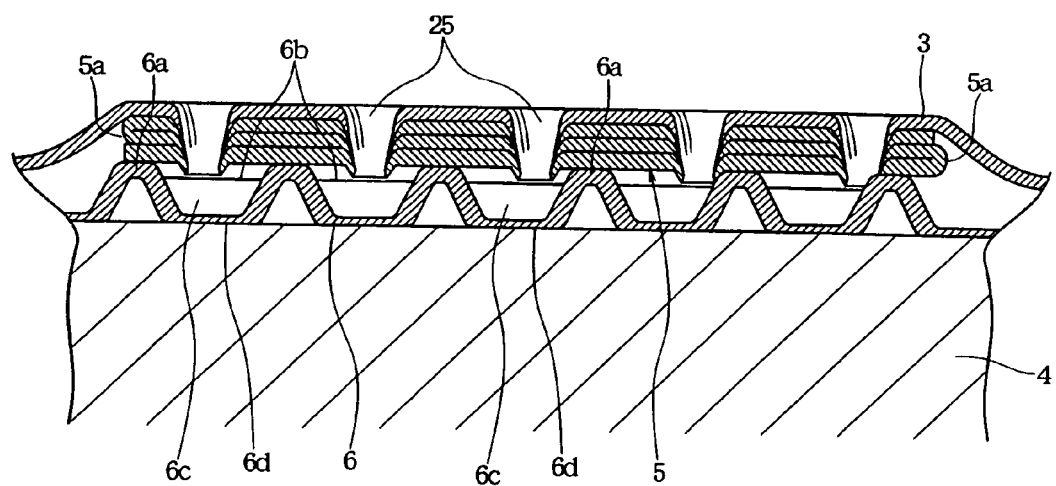
FIG. 3 is an enlarged sectional view showing how liquid passage holes are apertured and how a liquid acquisition layer is disposed.
Figure 4:
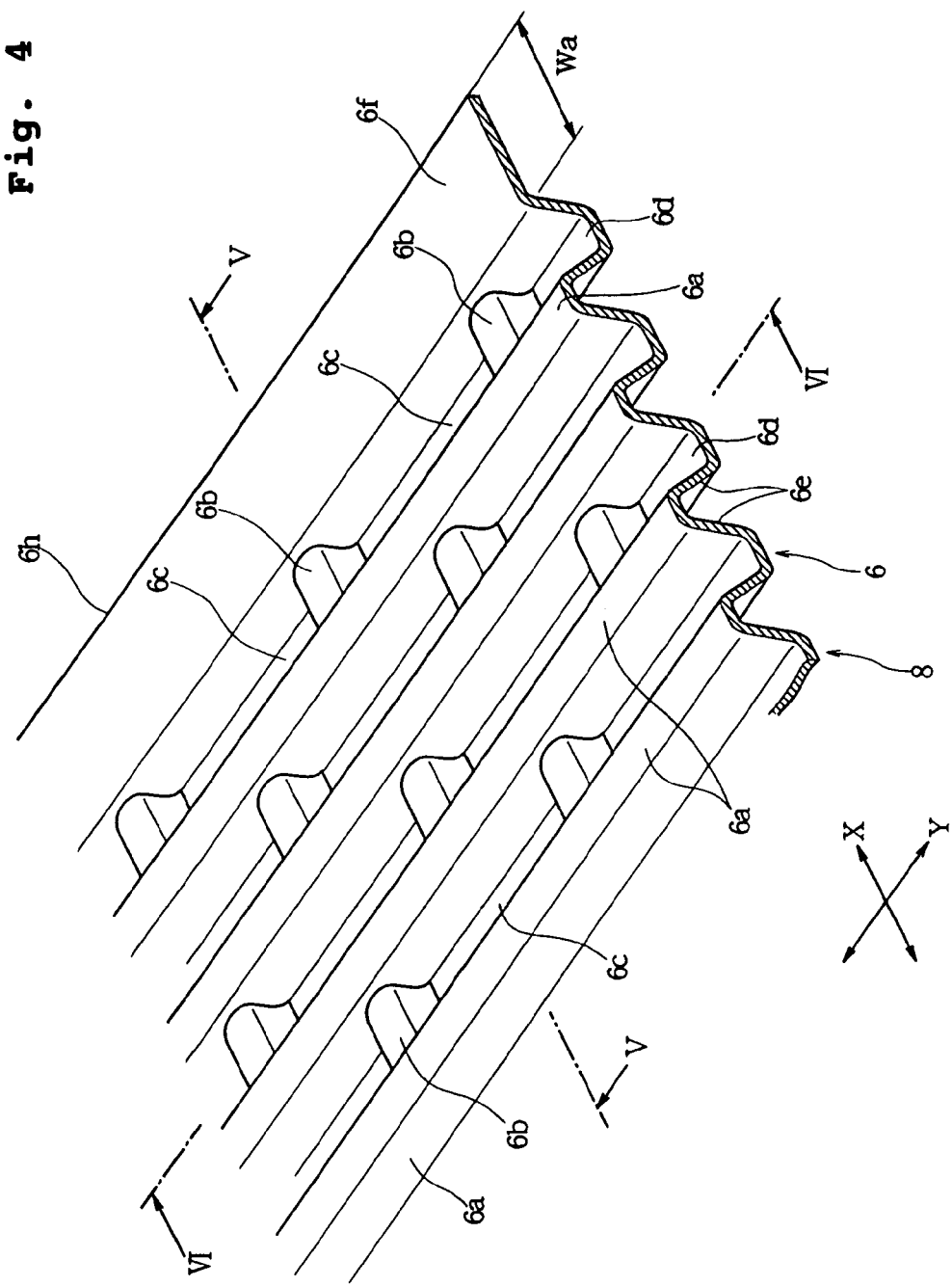
FIG. 4 is a perspective view of the liquid acquisition layer.

FIG. 1 is a top plan view showing a sanitary napkin 1 as an absorbent article according to a first embodiment of the present invention, wherein the skin surface faces upward; FIG. 2 is a sectional view taken along line II—II (transverse reference line), showing a state where the sanitary napkin of FIG. 1 is attached to a groin piece of an undergarment; FIG. 3 is an enlarged sectional view showing a central region of the sanitary napkin; FIG. 4 is a perspective view showing a liquid acquisition layer; FIGS. 5A and 5B are sectional views taken along line V—V of FIG. 4; and FIG. 6 is a sectional view taken along line VI—VI of FIG. 4.

The sanitary napkin 1 has longitudinally extending right and left side edges 1a and 1b that are transversely spaced an equal distance apart from a longitudinal centerline Oy—Oy and outwardly curved front and rear end edges 1c and 1d that are longitudinally spaced an equal distance apart from a transverse reference line Ox—Ox.

Within a range having a given length in the longitudinal direction and containing the transverse reference line Ox—Ox, the right and left side edges 1a and 1b project transversely outwardly, thereby providing wings 1A and 1A.

As shown in the sectional view of FIG. 2, the sanitary napkin 1 comprises a liquid-impermeable backsheet 2 appearing on the garment surface and a liquid-permeable topsheet 3 appearing on the skin surface. Between the backsheet 2 and the topsheet 3, a liquid absorbent layer 4 is disposed. A liquid permeable layer 5 is disposed beneath the topsheet 3, and a liquid acquisition layer 6 is disposed between the liquid permeable layer 5 and the liquid absorbent layer 4.

In the sanitary napkin 1, compressed groove 10 is formed in the skin surface by locally pressing and heating at least the topsheet 3 and the liquid absorbent layer 4. More specifically, the compressed groove 10 is formed by embossing with a heating roller. The compressed groove 10 may be formed such that after the liquid absorbent layer 4 is stacked on the topsheet 3, a smooth surface heating roller is applied to a surface of the liquid absorbent layer 4 while a heating roller having projections arranged in a pattern for embossing is applied to a surface of the topsheet 3 for pressing and heating.

In the compressed groove 10, high-density compressed portions, in which the liquid absorbent layer 4 and the topsheet 3 are pressed until they get almost filmy, and medium-density compressed portions, in which although doesn't get filmy, the liquid absorbent layer 4 is of a higher density than in portions other than the compressed groove 10, alternate with each other. The compressed groove 10 composed of the high-density compressed portions and the medium-density compressed portions is formed as grooves where the skin surface of the sanitary napkin 1 is recessed toward the side of the backsheet 2.

As shown in FIG. 1, the compressed groove 10 has several distinct compressed grooves indicated by numerals 11–16.

Longitudinally extending inner compressed grooves 11 and 11 are transversely spaced an equal distance apart from the longitudinal centerline Oy—Oy. The inner compressed grooves 11 and 11 are curved toward the longitudinal centerline Oy—Oy so that its separation distance becomes smallest at the transverse reference line Ox—Ox. The inner compressed grooves 11 and 11 are connected to each other through front and rear connecting compressed grooves 12 and 13. The front connecting compressed groove 12 is curved toward the front end edge 1c, while the rear connecting compressed groove 13 is curved toward the rear end edge 1d.

From boundaries between the inner compressed grooves 11 and 11 and the front connecting compressed groove 12, forwardly extending compressed grooves 14 and 14 are further extended toward the front end edge 1c. The forwardly extending compressed grooves 14 and 14 are transversely spaced an equal distance apart from the longitudinal centerline Oy—Oy. From boundaries between the inner compressed grooves 11 and 11 and the rear connecting compressed groove 13, on the other hand, rearwardly extending compressed grooves 15 and 15 are further extended toward the rear end edge 1*d*. The rearwardly extending compressed grooves 15 and 15 are transversely spaced an equal distance apart from the longitudinal centerline Oy—Oy.

The inner compressed grooves 11 and 11, the front connecting compressed groove 12, the rear connecting compressed groove 13, the forwardly extending compressed grooves 14, 14 and the rearwardly extending compressed grooves 15, 15 are mutually connected. Here, a given area of the skin surface of the sanitary napkin 1 is surrounded by the inner compressed grooves 11 and 11, the front connecting compressed groove 12 and the rear connecting compressed groove 13, and this surrounded area is referred to as central region 20. This central region 20 is of a shape symmetrical about the longitudinal centerline Oy—Oy and about the transverse reference line Ox—Ox.

Transversely outside the inner compressed grooves 11 and 11, there are provided outer compressed grooves 16 and 16. The outer compressed grooves 16 and 16 are formed within a range having a given length forwardly and rearwardly from the transverse reference line Ox—Ox. The outer compressed grooves 16 and 16 are curved similarly to the inner compressed grooves 11 and 11 while being spaced a constant distance apart from the inner compressed grooves 11 and 11.

As shown in FIG. 1, the liquid permeable layer 5 is given the shape of a strip elongated in the longitudinal direction, and right and left side edges 5*a* and 5*a* are spaced inwardly apart from the inner compressed grooves 11 and 11 so as not to overlap with the inner compressed grooves 11 and 11. The liquid permeable layer 5 reaches the front end edge 1*c* beyond the front connecting compressed groove 12 and also reaches the rear end edge 1*d* beyond the rear connecting compressed groove 13. In portions of the front and rear connecting compressed grooves 12 and 13, accordingly, the topsheet 3, the liquid permeable layer 5 and the liquid absorbent layer 4 are compressed together.

The liquid acquisition layer 6 is rectangular, and near the transverse reference line Ox—Ox, right and left side edges 6*h* and 6*h* are spaced transversely outwardly apart from the inner compressed grooves 11 and 11. On the other hand, front and rear end edges 6*i* and 6*j* are spaced longitudinally inwardly apart from the front and rear connecting compressed grooves 12 and 13. In portions of the inner compressed grooves 11 and 11, accordingly, the topsheet 3, the liquid acquisition layer 6 and the liquid absorbent layer 4 are compressed together.

In the central region 20, a large number of liquid passage holes 25 are regularly arranged. The liquid passage holes 25 are formed to pass through the topsheet 3 and reach the liquid permeable layer 5, and preferably, the liquid passage holes 25 are formed to pass through both the topsheet 3 and the liquid permeable layer 5, as shown in FIG. 3. In portions outside the side edges 5*a*, 5*a* of the liquid permeable layer 5, on the other hand, the liquid passage holes 25 are formed only in the topsheet 3.

The liquid passage hole 25 has an opening area of 0.2 to 8 mm$^2$, and when the liquid passage hole 25 is circle as in the present embodiment, it has a diameter of 0.5 to 3.2 mm. The center-to-center distance between adjacent liquid passage holes 25 is 1.5 to 8 mm.

Both the topsheet 3 and the liquid permeable layer 5 comprise heat-fusible, thermoplastic fibers. The liquid passage holes 25 can be formed in such a way that after the topsheet 3 and the liquid permeable layer 5 are stacked, heated needles or pins are inserted in a direction from the topsheet 3 to the liquid permeable layer 5 and then drawn out. At this time, the thermoplastic fibers contained in the topsheet 3 and the thermoplastic fibers contained in the liquid permeable layer 5 are fusion-bonded together along inner surfaces of the liquid passage holes 25 and therearound. This results in that the opening shape of the liquid passage hole 25 becomes stable and that the portion around the opening of the liquid passage hole 25 is reinforced with the liquid permeable layer 5. In addition, since the topsheet 3 and the liquid permeable layer 5 are thermally fusion-bonded together, there is no need for bonding the topsheet 3 and the liquid permeable layer 5 together through an adhesive, precluding the possibility that the adhesive will interfere with liquid permeation.

The topsheet 3 may be through-air bonded nonwoven fabric. For the through-air bonded nonwoven fabric, sheath/core bicomponent synthetic fibers, of which the core component is polyethylene terephthalate (PET) containing titanium oxide and the sheath component is polyethylene (PE), are bonded together by means of hot air to have a basis weight of about 15 to 60 g/m$^2$. It should be noted that some of the bicomponent synthetic fibers used for the topsheet 3 are coated with a hydrophilic lubricant while the rest are coated with a water-repellent lubricant and they are blended with each other, wherein the blending ratio of the fibers coated with the water-repellent lubricant is 10 to 30% by weight. With the fibers coated with the water-repellent lubricant uniformly contained in the topsheet 3 to have a blending ratio within the above-mentioned range, menstrual blood given to the topsheet 3 can be prevented from being excessively diffused in the topsheet 3, so that menstrual blood can be introduced into the liquid absorbent layer 4 mainly through the liquid passage holes 25.

It should be noted that also in regions other than the liquid passage holes 25, menstrual blood can permeate through the topsheet 3 into the liquid permeable layer 5. In order to provide the topsheet 3 with such permeability to liquid, the density of the topsheet 3 is preferably equal to or less than 0.12 g/cm$^3$, wherein the lower limit is about 0.025 g/cm$^3$.

The liquid permeable layer 5 may be through-air bonded nonwoven fabric comprising sheath/core bicomponent synthetic fibers, of which the core component is polypropylene (PP) and the sheath component is polyethylene (PE). In the through-air bonded nonwoven fabric for the liquid permeable layer 5, all the fibers are coated with a hydrophilic lubricant. That is, fibers coated with a water-repellent lubricant are not contained. In the embodiment shown in FIG. 3, the liquid permeable layer 5 is formed by stacking a plurality of layers of the through-air bonded nonwoven fabric, such as by folding a single through-air bonded nonwoven fabric in two- or three- or four-ply construction. The single through-air bonded nonwoven fabric has a basis weight in the range of about 15 to 50 g/m$^2$, so that the liquid permeable layer 5 preferably has a basis weight in the range of about 30 to 150 g/m$^2$, more preferably in the range of 50 to 100 g/m$^2$.

With the basis weight of the liquid permeable layer 5 made higher than the basis weight of the topsheet 3, the topsheet 3 of a low basis weight and a low density can be reinforced, thereby preventing occurrence of extremely large wrinkles in the topsheet 3 and occurrence of breakage from the liquid passage holes 25.

The fiber density of the liquid permeable layer 5 is lower than the fiber density of the topsheet 3 and in the range of 0.016 to 0.08 g/cm$^3$. For example, the topsheet 3 may comprise fibers having a fineness of 2.2 dtex while the liquid permeable layer 5 may comprise fibers having a fineness of 4.4 dtex. Since the density of the liquid permeable layer 5 is lower than that of the topsheet 3 and the liquid permeable layer 5 comprises fibers having a high fineness, the liquid permeable layer 5 can exhibit cushioning properties. With the liquid permeable layer 5 disposed within the range of a constant width that is symmetrical about the longitudinal centerline Oy—Oy, therefore, this range can softly contact the wearer's body.

The liquid acquisition layer 6 is manufactured by three-dimensionally shaping an absorbent sheet 8 that is provided with liquid absorbency, liquid permeability and shape retention ability, as shown in FIG. 4. In the present embodiment, the absorbent sheet 8 comprises cellulosic fibers and synthetic resin fibers. In the present embodiment, more specifically, the absorbent sheet 8 is air-laid nonwoven fabric (air-laid pulp), in which the cellulosic fibers are chemical pulp and the synthetic resin fibers are sheath/core bicomponent synthetic fibers of which the core component is polyethylene terephthalate (PET) and the sheath component is polyethylene (PE). The air-laid pulp is manufactured by accumulating the fibers in air into the form of a web, and adding a binder such as ethylene-vinyl acetate copolymer emulsion to form a sheet with a binder content of 5–20% by weight.

In order that menstrual blood absorbed in the liquid acquisition layer 6 can be smoothly transferred into the liquid absorbent layer 4, it is preferred that the absorbent sheet 8 contains the chemical pulp in an amount of at least 20% of the total weight of the fibers. In order to maintain the three-dimensional shape shown in FIG. 4 even in a wet state where menstrual blood is applied thereto, it is also preferred that the absorbent sheet 8 contains the synthetic resin fibers in an amount of at least 20% of the total weight of the fibers. Therefore, the weight ratio of the chemical pulp constituting the absorbent sheet to the synthetic resin fibers constituting the absorbent sheet is preferably from 80:20 to 20:80.

In order to maintain the liquid acquisition layer 6 in the three-dimensional state shown in FIG. 4, the basis weight of the absorbent sheet 8 is preferably in the range of 20 to 200 g/m². For the absorbent sheet 8 having a basis weight within this range, the air-laid nonwoven fabric may be used in a single-ply construction or may be folded in two- or three-ply construction.

In both the X-direction and the Y-direction, the liquid acquisition layer 6 that is in the three-dimensional shape of FIG. 4 preferably has a dry tensile breaking strength of at least 2.5 N/25 mm width. The tensile breaking strength is expressed by a maximum load measured when a chuck-to-chuck distance is increased at a rate of 100 mm/min, wherein a specimen of the liquid acquisition layer 6 is prepared as a strip elongated in the X- or Y-direction to have a width of 25 mm and held by chucks to have an original chuck-to-chuck distance of 100 mm. It should be noted that wet tensile breaking strength of the liquid acquisition layer 6, as measured in a wet state where the liquid acquisition layer 6 is applied artificial menstrual blood that will be described later, is preferably at least 20%, more preferably at least 30% of the dry tensile breaking strength.

With the basis weight and the tensile breaking strength set within the above-mentioned ranges, the liquid acquisition layer 6 can be certainly maintained in the three-dimensional shape in both dry and wet states, so that the recesses of the liquid acquisition layer 6 can exhibit the function of retaining menstrual blood repeatedly applied thereto. If the basis weight and the tensile breaking strength can be set within the above-mentioned ranges, the liquid acquisition layer 6 may be formed of various materials other than the above-identified air-laid nonwoven fabric.

For example, there may be used air-laid nonwoven fabric manufactured by bonding only pulp with a binder. Spunlaced nonwoven fabric manufactured by entangling cellulosic fibers and synthetic resin fibers with water jets may also be used. It is also possible to use a composite sheet prepared by integrating spunlaced nonwoven fabric mainly composed of at least one of pulp and rayon being cellulosic fibers with through-air bonded nonwoven fabric mainly composed of synthetic resin fibers by water-jet treatment or heat-sealing. Similarly, the spunlaced nonwoven fabric may be integrated with point-bonded or spunbonded nonwoven fabric. Alternatively, the spunlaced nonwoven fabric may be bonded to an apertured film.

In the case where the liquid acquisition layer 6 comprises a various kinds of fibers, if the cellulosic fiber content is higher on the side directed to the liquid permeable layer 5 than on the side directed to the liquid absorbent layer 4, menstrual blood can be easily drawn in from the liquid permeable layer 5 into the liquid acquisition layer 6. On the other hand, if the cellulosic fiber content is higher on the side directed to the liquid absorbent layer 4, menstrual blood can be easily transferred into the liquid absorbent layer 4.

As shown in FIG. 4, the liquid acquisition layer 6 has longitudinal ribs 6a that are deformed to project toward the topsheet 3 and transverse ribs 6b that are also deformed to project toward the topsheet 3. The longitudinal ribs 6a are linearly extended in the longitudinal direction (Y-direction) and arranged at regular intervals in the transverse direction (X-direction) in parallel relationship with each other. The transverse ribs 6b are formed to connect adjacent longitudinal ribs 6a. The transverse ribs 6b are arranged in rows, and in each row, the transverse ribs 6b are arranged at regular intervals in the longitudinal direction in parallel relationship with each other. Between adjacent rows, however, adjacent transverse ribs 6b are not aligned with each other in the transverse direction, i.e., transverse ribs 6b of one row are offset with respect to transverse ribs 6b of an adjacent row.

The liquid acquisition layer 6 is recessed toward the liquid absorbent layer 4 at portions surrounded by the longitudinal ribs 6a and the transverse ribs 6b, wherein these recesses defined by the longitudinal ribs 6a and the transverse ribs 6b are indicated by 6c. The recesses 6c are elongated to be longer in the Y-direction than in the X-direction. Thus, a large number of the recesses 6c are regularly arranged in the liquid acquisition layer 6.

The liquid acquisition layer 6 has flat portions 6f, 6f that are of a constant width Wa inwardly from both side edges 6h, 6h. In these flat portions 6f, 6f, the recesses 6c are not formed. The flat portions 6f are wider than the longitudinal ribs 6a, whose width will be described hereinafter. Concretely, the width Wa of the flat portions 6f is preferably 1.2 to 10 times, more preferably 2 to 5 times of the width of the longitudinal ribs 6a. In the present embodiment, the flat portions 6f, 6f are provided in both side portions of the liquid acquisition layer 6 and the recesses 6c are regularly arranged in the entire area positioned between the flat portions 6f, 6f. In an alternative, such flat portions may be provided in both end portions of the liquid acquisition layer 6 to have a given width inwardly from front and rear end edges 6i, 6j. In this case, the width of the flat portions measured from the front and rear end edges 6i, 6j is preferably 1.2 to 10 times, more preferably 2 to 5 times of the width of the transverse ribs 6b.

As shown in FIG. 6, a height h1 from the lower surfaces of the recesses 6c to the tops of the longitudinal ribs 6a is greater than a height h2 from the lower surfaces of the recesses 6c to the tops of the transverse ribs 6b. As shown in FIG. 3, the tops of the longitudinal ribs 6a are brought into contact with and bonded to the lower surface of the liquid permeable layer 5 through a hot-melt adhesive, while the lower surfaces of the recesses 6c are bonded to the upper surface of the liquid absorbent layer 4 through a hot-melt adhesive. That is, the tops of the longitudinal ribs 6a lie on the same plane so as to come into contact with the liquid permeable layer 5, and the lower surfaces of the recesses 6c lie on the same plane so as to come into contact with the liquid absorbent layer 4. Here, the flat portions 6f, 6f of the liquid acquisition layer 6 are also bonded to the lower surface of the liquid permeable layer 5 through a hot-melt adhesive.

The hot-melt adhesive is randomly applied to a portion of the lower surface of the liquid acquisition layer 6 and to a portion of the upper surface of the liquid absorbent layer 4 so that the hot-melt adhesive will not interfere with permeation of menstrual blood from the liquid permeable layer 5 into the liquid acquisition layer 6 and further from the liquid acquisition layer 6 into the liquid absorbent layer 4.

As set forth above, since the tops of the transverse ribs 6b are positioned lower than the tops of the longitudinal ribs 6a, at least some of the tops of the transverse ribs 6b remain unbonded to the liquid permeable layer 5, leaving a small space between the tops of the transverse ribs 6b and the liquid permeable layer 5.

As will be described hereinafter, the liquid acquisition layer 6 is three-dimensionally shaped by holding the flat absorbent sheet 8 between molding rollers. Since tensile stress is concentrated at walls 6e of the recesses 6c during the three-dimensional shaping, a force to separate fibers from each other is exerted on the walls 6e so that low-density portions having a lower fiber density than the tops of the longitudinal ribs 6a, the tops of the transverse ribs 6b, the bottoms 6d of the recesses 6c, can be produced in the walls 6e. In addition, the concentration of tensile stress may sometimes cause breakage in the walls 6e. At the tops of the longitudinal ribs 6a and at the bottoms 6d of the recesses 6c, on the other hand, the fibers constituting the absorbent sheet 8 are compressed to have an increased fiber density. Furthermore, since no pressure is exerted on the flat portions 6f during molding, the flat portions 6f have a lower density than the tops of the longitudinal ribs 6a and the bottoms 6d of the recesses 6c.

It should be noted that the mean density of the liquid acquisition layer 6 is higher than those of the topsheet 3 and the liquid permeable layer 5, but lower than the fiber density of the underlying liquid absorbent layer 4. Since the longitudinal ribs 6a of the liquid acquisition layer 6 are in contact with the liquid permeable layer 5 and the bottoms 6d of the recesses 6c are in contact with the liquid absorbent layer 4, menstrual blood can easily be transferred from the topsheet 3, through the liquid permeable layer 5 into the liquid acquisition layer 6 and further from the liquid acquisition layer 6 into the liquid absorbent layer 4 due to the density gradient. Furthermore, since the walls 6e of the recesses 6c of the liquid acquisition layer 6 are provided with the low-density portions, in which fibers are separated from each other or breakage is caused, as set forth above, menstrual blood temporarily retained by the recesses 6c can be rapidly transferred into the liquid absorbent layer 4.

In order that menstrual blood can be rapidly transferred from the liquid permeable layer 5 into the liquid acquisition layer 6 and further from the liquid acquisition layer 6 into the liquid absorbent layer 4, the mean density of the liquid acquisition layer 6 is preferably in the range of 0.05 to 0.25 g/m$^3$, while the fiber density of the liquid absorbent layer 4 beneath the liquid acquisition layer 6 is preferably in the range of 0.07 to 0.25 g/m$^3$.

The longitudinal ribs 6a have a width in the range of 2 to 10 mm, preferably in the range of 2 to 6 mm, at a height of (½)×h1, while the transverse ribs 6b have a width in the range of 2 to 10 mm, preferably in the range of 2 to 6 mm, at a height of (½)×h2. The height h1 of the liquid acquisition layer 6 is in the range of 1.3 to 5 mm. In order to retain a sufficient amount of menstrual blood having passed through the topsheet 3 by the recesses 6c, it is preferred that each recess 6c has an opening area in the range of 5 to 20 mm$^2$ at a height of (½)×h2 and that the space volume of each recess 6c, expressed by {opening area×(height h1−thickness of absorbent sheet)}, is in the range of 8 to 80 mm$^3$.

On the other hand, the aspect ratio (i.e., ratio of the dimension in the Y-direction to the dimension in the X-direction) of each recess 6c at a height of (½)×h2 is preferably in the range of 1.1 to 10, more preferably in the range of 1.5 to 7, most preferably in the range of 2 to 5. If the aspect ratio is smaller than the above-mentioned range, the function of leading menstrual blood acquired by the liquid acquisition layer 6 along the longitudinal direction will be deteriorated to thereby increase the possibility of diffusion in the transverse direction; if the aspect ratio is in excess of the above-mentioned range, on the other hand, the transverse ribs 6b are separated so far away from each other that when a compressive force in the transverse direction is applied from the thighs or the like, a sufficient elastic restoring force in the transverse direction will not be exhibited.

In the liquid acquisition layer 6, the transverse ribs 6b are arranged at intervals in the longitudinal direction. Therefore, when a bending force is so exerted on the sanitary napkin 1 as to recess the skin surface with the front and rear end edges 1c and 1d approaching each other, the liquid acquisition layer 6 can be easily bent to follow the deformation. Particularly when the aspect ratio of each recess 6c is in the above-mentioned range, the liquid acquisition layer 6 can be bent easily in the above-identified direction. Since the liquid acquisition layer 6 can follow the bending deformation of the sanitary napkin 1, easy separation of the liquid acquisition layer 6 from the liquid permeable layer 5 can be prevented.

Since the transverse ribs 6b are staggered with respect to each other in the transverse direction (X-direction), as shown in FIG. 4, the liquid acquisition layer 6 can be easily bent in the longitudinal direction, as set forth above. Moreover, since the height h2 of the transverse ribs 6b is smaller than the height h1 of the longitudinal ribs 6a, the side edges 6h, 6h of the liquid acquisition layer 6 can easily approach each other with the skin surface concavely deformed.

The liquid absorbent layer 4 may be formed by adding synthetic absorbent polymer such as polyacrylate, polyacrylamide and maleic anhydride or natural absorbent polymer such as starch and cellulose to an aggregate of pulp such as ground pulp, mercerized pulp or crosslinked pulp, wherein the pulp and the synthetic absorbent polymer or the like are wrapped in hydrophilic tissue paper.

The backsheet 2 is a liquid-impermeable, breathable sheet such as a polyethylene (PE) or polypropylene (PP) film formed with minute pores. The minute pores may be appropriately distributed over the film for improving breathability such as by adding inorganic filler such as $CaCO_3$ and $BaSO_4$ to the plastic sheet, followed by drawing. The film may have a thickness of about 15 to 50 μm.

As shown in FIG. 2, liquid-impermeable sheets 30 and 30 are provided on right and left side portions of the skin surface. In the wings 1A, 1A, the liquid-impermeable sheets 30 and 30 are bonded to the backsheet 2 through a hot-melt adhesive. At positions transversely spaced an equal distance apart from the longitudinal centerline Oy—Oy, the liquid-impermeable sheets 30, 30 are folded in two with longitudinally extending elastic members 32 bonded to the inside. Due to the elastic members 32, an elastic shrinkage force acts between front and rear portions of the sanitary napkin 1 to curve the sanitary napkin 1, which results in rising of the liquid-impermeable sheets 30 and 30 at an intermediate portion between the front and rear portions of the sanitary napkin 1, thereby forming leakage preventing walls 31 and 31.

The liquid-impermeable sheets may be spunbonded nonwoven fabric, meltblown nonwoven fabric, or composite nonwoven fabric being a laminate thereof.

The basis weight of the liquid absorbent layer 4 becomes largest at the central region 20. The basis weight at the portions located between the inner compressed grooves 11, 11 and the outer compressed grooves 16, 16, is lower than that at the central region 20. The basis weight of the liquid absorbent layer 4 at the other portions is equal to or slightly lower than that at the portions located between the inner compressed grooves 11, 11 and the outer compressed grooves 16, 16.

The basis weight of the liquid absorbent layer 4 at the central region 20 is preferably in the range of 400 to 1200 $g/m^2$, more preferably in the range of 500 to 1000 $g/m^2$. The basis weight at the portions located between the inner compressed grooves 11, 11 and the outer compressed grooves 16, 16 is preferably in the range of 300 to 900 $g/m^2$, more preferably in the range of 350 to 600 $g/m^2$. The basis weight of the liquid absorbent layer 4 at the other portions is preferably in the range of 200 to 700 $g/m^2$, more preferably in the range of 300 to 500 $g/m^2$.

As a result, the thickness is increased in the central region 20 so that the skin surface bulges toward the wearer's body in the central region 20, as shown in FIG. 2.

The length of the central region 20, i.e., the longitudinal distance between the front connecting compressed groove 12 and the rear connecting compressed groove 13 is equal to or greater than 50 mm. The width W1 of the central region 20 on the transverse reference line Ox—Ox shown in FIG. 2 is decided according to the width of the woman's genital organ. Because the crotch width of average women is about 30 mm, the width W1 is preferably in the range of 15 to 50 mm, more preferably in the range of 20 to 40 mm.

When the sanitary napkin 1 is to be attached to the wearer's body, a pressure-sensitive adhesive provided on the exterior surface of the backsheet 2 is adhered to the inner side of a groin piece 26 shown in FIG. 2, and then, the wings 1A, 1A are folded back against an outer side of the undergarment to cover both side edges of the groin piece 26, and adhered to the outer side of the groin piece 26 through a pressure-sensitive adhesive provided on the garment surface of the wings 1A, 1A.

In the sanitary napkin 1, since the central region 20 bulges toward the wearer's body as shown in FIG. 2, the central region 20 easily comes into close contact with the vaginal opening. Here, the topsheet 3 appearing on the skin surface in the central region 20 is through-air bonded nonwoven fabric of a low density and the liquid permeable layer 5 provided beneath it is bulky through-air bonded nonwoven fabric. Therefore, the central region 20 can softly contact the wearer's body.

Menstrual blood discharged from the vaginal opening is mainly applied to the central region 20. Since the topsheet 3 is nonwoven fabric of a low density, menstrual blood can permeate through the topsheet 3. However, diffusion of menstrual blood in the topsheet 3 is inhibited because the topsheet 3 contains the fibers coated with the water-repellent lubricant. Since the liquid permeable layer 5 positioned beneath the topsheet 3 is through-air bonded nonwoven fabric having voids therein, menstrual blood is allowed to pass through the voids formed in the liquid permeable layer 5 under gravitation and fall into the underlying liquid acquisition layer 6. However, most of menstrual blood given to the central region 20 rapidly passes through the liquid passage holes 25 and directly falls into the liquid acquisition layer 6.

Menstrual blood having fallen into the liquid acquisition layer 6 is absorbed by the absorbent sheet 8 forming the liquid acquisition layer 6 and then transferred into the underlying liquid absorbent layer 4. If a large amount of menstrual blood is applied to the topsheet 3 at a time, the menstrual blood passes through the liquid passage holes 25 and falls into the liquid acquisition layer 6, wherein the menstrual blood can be retained on the spot by the recesses 6c formed in the liquid acquisition layer 6. Therefore, even if a large amount of menstrual liquid is discharged, it will not remain in either the topsheet 3 or the liquid permeable layer 5 for a long period of time. In the central region 20, accordingly, the skin surface can be kept in a nearly dry state, hardly causing wet feeling and stuffy feeling in the wearer's crotch.

Menstrual blood applied to the recesses 6c of the liquid acquisition layer 6 can be rapidly introduced into the liquid absorbent layer 4 through the bottoms 6d of the recesses 6c and through the low-density or broken portions formed in the walls 6e of the recesses 6c. If menstrual blood is applied to some of the recesses 6c in an amount in excess of the space volume, furthermore, menstrual blood can move to adjacent recesses 6b in the longitudinal direction beyond the relatively low transverse ribs 6b. On the other hand, since the longitudinal ribs 6a extending parallel with each other in the longitudinal direction to define two sides of each recess 6c have the tops kept in contact with and bonded to the liquid permeable layer 5, menstrual blood in the liquid acquisition layer 6 will be hardly diffused in the transverse direction. Therefore, menstrual blood applied in a large amount can be absorbed by the liquid absorbent layer 4 while being transferred sequentially to adjacent recesses 6c arranged in the longitudinal direction.

Furthermore, the right and left side portions of the liquid acquisition layer 6 are formed as the longitudinally extending flat portions 6f, 6f that are of a lower fiber density than the longitudinal ribs 6a. Therefore, even if menstrual blood is diffused along the liquid acquisition layer 6 in the transverse direction (X-direction), it can be blocked by the flat portions 6f, 6f. Thus, the possibility of leakage in the transverse direction can be reduced.

Should menstrual blood be diffused farther in the transverse direction toward or across the side edges 6h, 6h of the liquid acquisition layer 6, the menstrual blood will be blocked by the inner compressed grooves 11, 11 or the outer compressed grooves 16, 16, thereby effectively preventing transverse liquid leakage from the sanitary napkin 1.

Since the absorbent sheet 8 forming the liquid acquisition layer 6 contains synthetic resin fibers, the three-dimensional shape can be maintained even in a wet state where menstrual blood is absorbed. In addition, when a pressure acting on the central region 20 from the wearer's crotch is eliminated, the liquid acquisition layer 6 can be restored to its original three-dimensional shape shown in FIG. 4. Particularly because the longitudinal ribs 6a and the transverse ribs 6b are provided, the liquid acquisition layer 6 is excellent in elastic restoring function.

Next, a method for manufacturing the sanitary napkin 1 will be described.

At first, a process for shaping the liquid acquisition layer 6 into the three-dimensional shape shown in FIG. 4 will be described.

Figure 7:
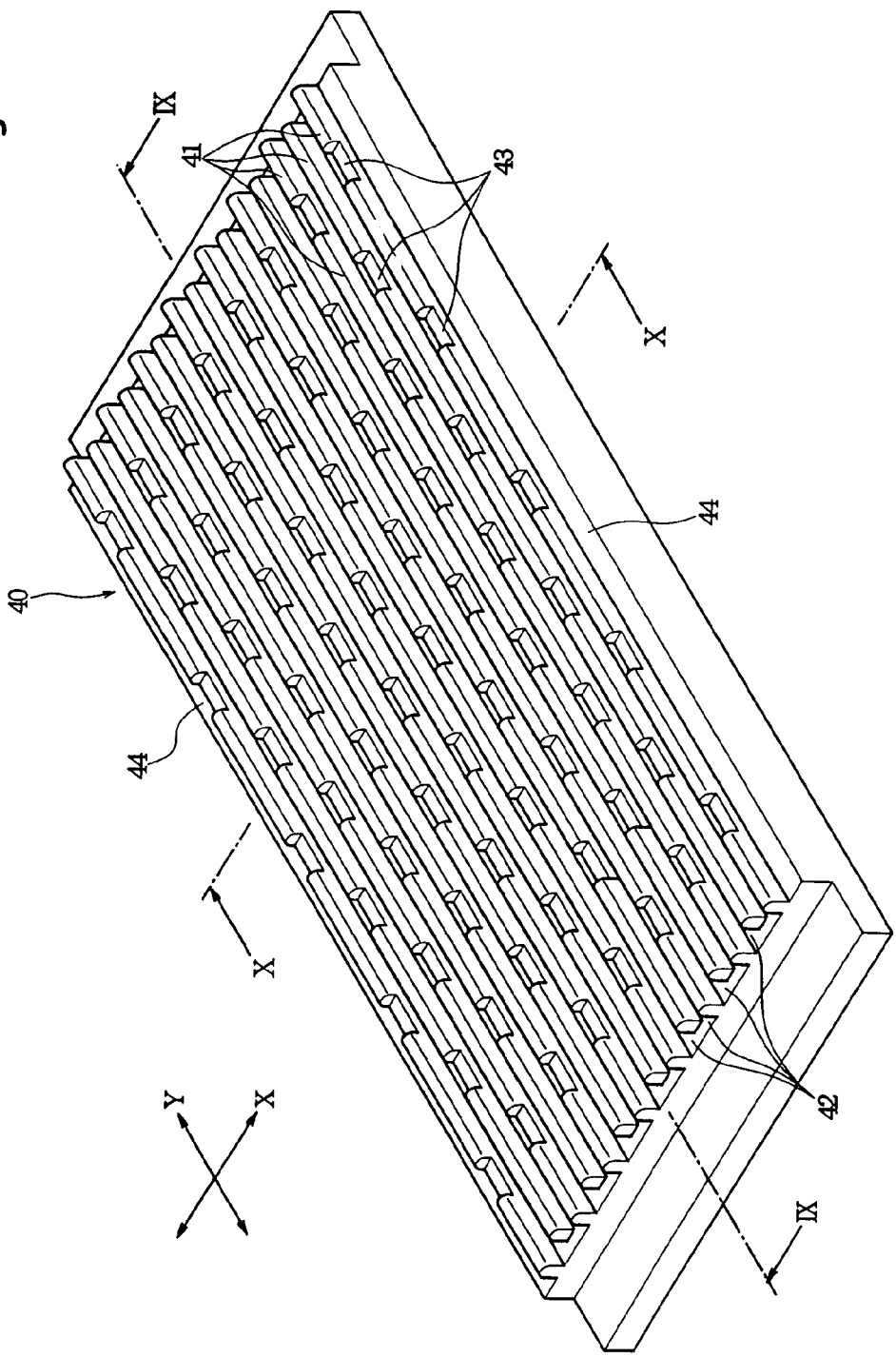
FIG. 7 is a perspective view showing an upper mold for three-dimensionally shaping the liquid acquisition layer.

FIG. 7 is a perspective view showing an upper mold 40 for shaping the liquid acquisition layer 6; FIG. 8 is a perspective view showing a lower mold 50; and FIG. 9 is a sectional view of the upper mold 40 taken along line IX—IX.

The upper mold 40 shown in FIG. 7 is formed with projections 41 arranged in rows and grooves 42 positioned between adjacent rows of the projections 41. The projections 41 and the grooves 42 extend parallel with each other in the longitudinal direction (Y-direction). In each row of the projections 41, recesses 43 are arranged at intervals in the longitudinal direction (Y-direction). That is, the projections 41 and the recesses 43 alternate with each other in the longitudinal direction. The recesses 43 arranged in one row of the projections 41 are positioned midway between adjacent recesses 43 arranged in an adjacent row of the projections 41. Between adjacent rows of the projections 41, therefore, the recesses 43 are staggered with respect to each other.

As shown in FIG. 9, longitudinally opposite ends 41a of each projection 41 are rounded off, and a height H1 from bottoms 42a of the grooves 42 to tops of the projections 41 is larger than a height H2 from the bottoms 42a to tops of the recesses 43.

The lower mold 50 shown in FIG. 8 is formed with projections 51 and grooves 52 positioned between adjacent projections 51. The projections 51 and the grooves 52 extend parallel with each other in the longitudinal direction (Y-direction). The projections 41 of the upper mold 40 are arranged at the same pitch in the transverse direction (X-direction) as the grooves 52 of the lower mold 50.

With both the mating surface of the upper mold 40 and the mating surface of the lower mold 50 heated to about 120 degrees centigrade that is lower than the melting point of polyethylene constituting the sheath component of the sheath/core bicomponent synthetic fibers, the absorbent sheet 8 is held between the upper mold 40 and the lower mold 50, as shown in FIG. 10. The upper mold 40 and the lower mold 50 mate with each other such that the projections 41 fit in the grooves 52 while the projections 51 fit in the grooves 42. It should be noted that the upper mold 40 is not pressed against the lower mold 50 in a mated condition so that a little clearance can be left between the tops of the projections 41 of the upper mold 40 and the bottoms of the grooves 52 of the lower mold 50 and a little clearance can be left between the tops of the projections 51 of the lower mold 50 and the bottoms of the grooves 42 of the upper mold 40.

As a result, the longitudinal ribs 6a are formed by the projections 51 of the lower mold 50 and the recesses 6c are formed by the projections 41 of the upper mold 40, as shown in FIG. 10. With the absorbent sheet 8 being lightly pressed by the recesses 43 of the upper mold 40, furthermore, the transverse ribs 6b are formed by the recesses 43.

The upper mold 40 has longitudinally extending flat portions 44, 44 at its both sides, while the lower mold 50 has longitudinally extending flat portions 53, 53 at its both sides. Between the flat portions 44, 44 and the flat portions 53, 53, the absorbent sheet 8 remains unpressed, providing the flat portions 6f, 6f.

The absorbent sheet 8 is held between the upper mold 40 and the lower mold 50 that are so installed as to leave a clearance therebetween in a mated condition and heated to a temperature slightly lower than the melting point of the bicomponent synthetic fibers. Since the absorbent sheet 8 is thus molded, the liquid acquisition layer 6 is never provided with filmy portions where fibers are completely melted and solidified to interfere with liquid permeation. Here, since the bicomponent synthetic fibers are heated almost to the melting point, the three-dimensional shape shown in FIG. 4 can be maintained after molding.

Since the recesses 6c of the liquid acquisition layer 6 are formed by pressing with the projections 41 that are of a given length and arranged at intervals in the longitudinal direction, tensile stress in both the X- and Y-directions is concentrated at portions of the absorbent sheet 8 that form the walls 6e of the recesses 6c. This results in increasing the fiber-to-fiber distance in the walls 6e of the recesses 6c, and sometimes causing breakage. At this time, since the longitudinal ribs 6a are formed by pressing with the projections 51 each extending continuously in the longitudinal direction, the fiber density can be increased at the tops of the longitudinal ribs 6a, and the fiber density can also be increased at the bottoms 6d of the recesses 6c. It should be noted that the fiber density at the tops of the transverse ribs 6b is also higher than that at the walls 6e.

When the liquid acquisition layer 6 is to be mass-produced, the upper mold 40 shown in FIG. 7 is formed on the surface of a roll with the Y-direction and the X-direction adapted to the circumferential direction and the axial direction, respectively; the lower mold 50 shown in FIG. 8 is also formed on the surface of another roll with the Y-direction and the X-direction adapted to the circumferential direction and the axial direction, respectively. These rolls are opposed to each other with a clearance left therebetween. The absorbent sheet 8 is fed in between the rolls, producing the liquid acquisition layer 6.

In a manufacturing process of the sanitary napkin 1, after the topsheet 3 and the liquid permeable layer 5 are stacked, the liquid passage holes 25 are formed therein. Subsequently, the longitudinal ribs 6a and the flat portions 6f, 6f of the liquid acquisition layer 6 are bonded to the lower surface of the liquid permeable layer 5 through a hot-melt adhesive. On the other hand, the lower surfaces of the recesses 6c of the liquid acquisition layer 6 are bonded to the liquid absorbent layer 4 through a hot-melt adhesive. After the topsheet 3, the liquid permeable layer 5, the liquid acquisition layer 6 and the liquid absorbent layer 4 are stacked, the compressed groove 10 is formed therein. Then, the backsheet 2 is laid on and bonded to the lower surface of the stack, and the liquid impermeable sheets 30 are bonded to stack so as to appear on the skin surface.

It should be noted that unlike the walls 6e of the recesses 6c, the flat portions 6f, 6f extending in the longitudinal direction at both sides of the liquid acquisition layer 6 are formed without increasing the fiber-to-fiber distance therein, so that they are of a certain degree of stiffness and a uniform density. During assembly of the sanitary napkin 1, accordingly, the liquid acquisition layer 6 may be transported while keeping its three-dimensional shape, such as by attracting the flat portions 6f, 6f onto a suction belt.

The liquid acquisition layer 6 may be formed of a single absorbent sheet 8, but may also be formed of a stack of two or more absorbent sheets 8. FIG. 5B shows a case where two absorbent sheets 8A and 8B are stacked for the liquid acquisition layer 6. The individual absorbent sheets 8A and 8B are formed of the same material as the absorbent sheet 8.

When the liquid acquisition layer 6 is three-dimensionally shaped, the fiber-to-fiber distance is increased due to tensile force exerted on the walls 6e of the recesses 6c, sometimes causing breakage, as described hereinabove. If the liquid acquisition layer 6 is formed of a stack of two or more absorbent sheets, however, the low-density or broken portions in the individual walls 6e may be located at different positions for different sheets. Therefore, the entire strength of each wall 6e of the recesses 6c can be prevented from being excessively decreased, so that the liquid acquisition layer 6 can be effectively restored to its original three-dimensional shape after it is flattened out by pressure from the body.

The two or more absorbent sheets may be partially bonded together. In the case where the two or more absorbent sheets all contain thermoplastic fibers, they may be bonded together by fusion-bonding of fibers. In an alternative, the absorbent sheets may be bonded together with an adhesive. When the liquid acquisition layer 6 is three-dimensionally shaped with heated molds as shown in FIGS. 7 to 10, the absorbent sheets may be bonded together by means of heat of the molds under such a degree of pressure as not to produce filmy portions. In another alternative, the two or more absorbent sheets may be thermally bonded together at dotted bonds prior to molding of the liquid acquisition layer 6 into the three-dimensional shape.

When two or more absorbent sheets are bonded together, bonded portions may be located at any of the longitudinal ribs 6a, the transverse ribs 6b, the walls 6e of the recesses 6c, and the bottoms 6d of the recesses 6c. Alternatively, the bonded portions may be randomly distributed in all these portions. However, it is preferred that the absorbent sheets are bonded together at least in the walls 6e of the recesses 6c.

If the bonded portions are provided in the longitudinal ribs 6a and the transverse ribs 6b, the network structure in the longitudinal ribs 6a and the transverse ribs 6b can be reinforced. On the other hand, the fiber density is extremely decreased in the walls 6e of the recesses 6c, as set forth above, but if the bonded portions are provided in the walls 6e, the recesses 6c can be increased in stiffness for maintaining its shape. If the bonded portions are provided in the bottoms 6d of the recesses 6c, on the other hand, the density can be increased in the bottoms 6d, resulting in that menstrual blood applied to the liquid acquisition layer 6 can be concentrated at the bottoms 6d of the recesses 6c for introduction into the liquid absorbent layer 4.

Figure 11:
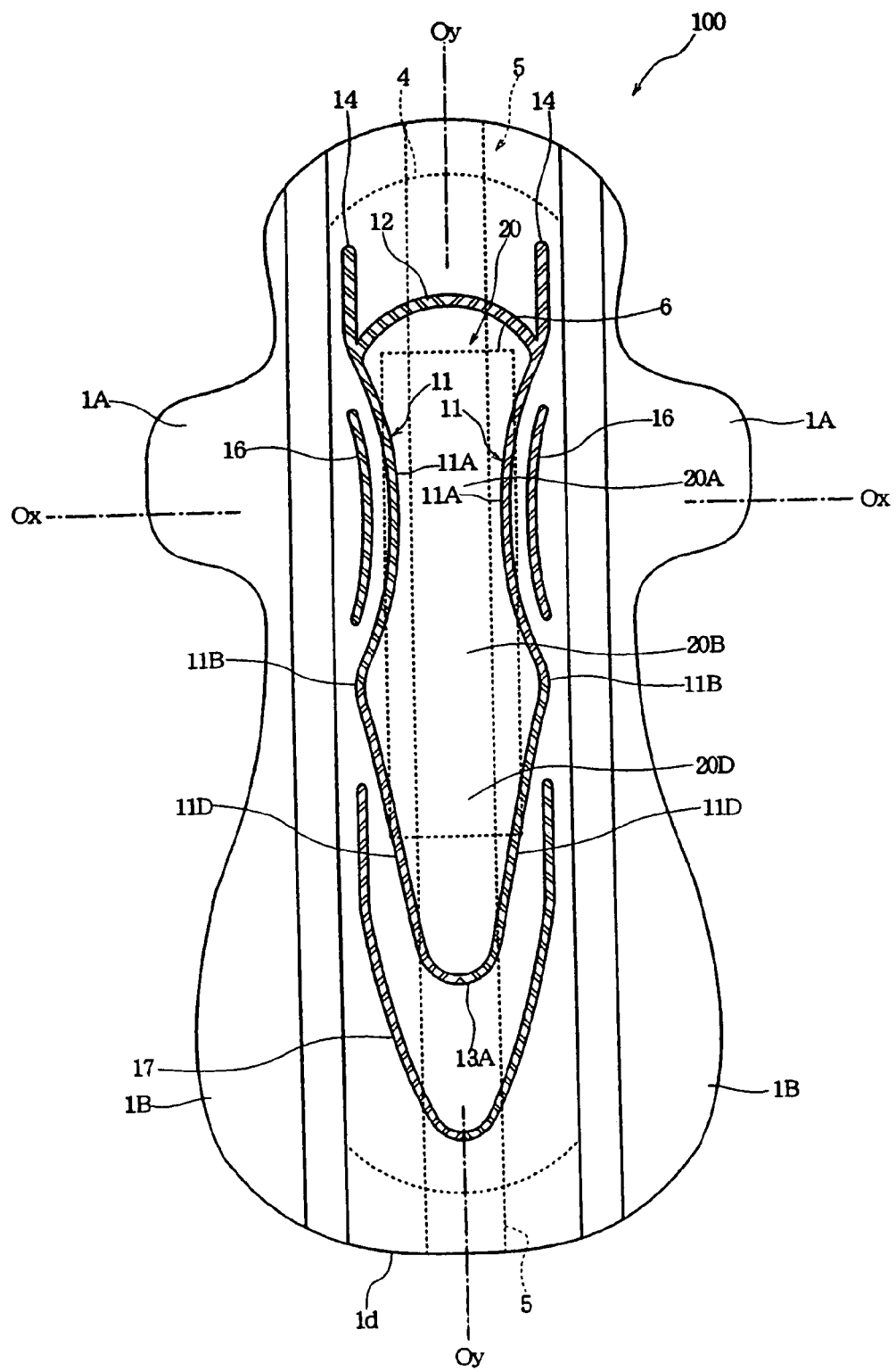
FIG. 11 is a top plan view showing an elongated sanitary napkin as an absorbent article according to a second embodiment of the present invention.

FIG. 11 is a top plan view showing a sanitary napkin 100 as an absorbent article according to a second embodiment of the present invention. Hereinafter, the detailed description of the portions having the same construction as those of the embodiment of FIG. 1 will be omitted by designating them by the common reference numerals.

The sanitary napkin 100 is a long type of sanitary napkin suitable for use during sleep, wherein the entire length in the longitudinal direction (Y-direction) is about 200 to 450 mm, and the right and left side edges 1a and 1b are gradually outwardly curved from positions rearward of the wings 1A and 1A toward the rear end edge 1d, thereby forming rear flaps 1B and 1B that are intended to come into contact with the wearer's buttocks.

In the skin surface, the inner compressed grooves 11, 11 are formed to include front portions 11A, 11A, inflected portions 11B, 11B, and rear portions 11D, 11D. The front portions 11A, 11A are curved toward the longitudinal centerline Oy—Oy. The separation distance between the inner compressed grooves 11, 11 becomes largest at the inflected portions 11B, 11B. The rear portions 11D, 11D gradually approach each other toward the rear end edge 1d and are connected to each other through a rear connecting compressed groove 13A.

The region surrounded by the inner compressed grooves 11, 11, the front connecting compressed groove 12 and the rear connecting compressed groove 13A is referred to as central region 20. In the central region 20, the region between the front portions 11A, 11A is referred to as front central region 20A that is intended to face the vaginal opening; the region between the inflected portions 11B, 11B is referred to as intermediate central region 20B that is intended to face the perineum; the region between the rear portions 111D, 11D is referred to as rear central region 20D that is intended to face the anus and the cleft of the buttocks.

Transversely outside the front portions 11A, 11A of the inner compressed grooves 11, 11, moreover, the outer compressed grooves 16, 16 are provided in the same manner as in FIG. 1. Transversely outside the rear portions 11D, 11D of the inner compressed grooves 11, 11, on the other hand, there are provided rear outer compressed grooves 17, 17 that are connected to each other inside the rear end edge 1d.

In the present embodiment, the liquid permeable layer 5 is given the shape of a strip to extend from the front end edge 1c to the rear end edge 1d, while the liquid acquisition layer 6 having the same three-dimensional shape as shown in FIG. 4 is provided in the central region 20.

In the present embodiment, the length of the central region 20, i.e., the longitudinal distance between the front connecting compressed groove 12 and the rear connecting compressed groove 13A is about 120 to 350 mm, wherein the liquid acquisition layer 6 should be present at least in the front central region 20A intended to face the vaginal opening. The liquid acquisition layer 6 may also be present in both the front central region 20A and the intermediate central region 20B intended to face the perineum, as shown in FIG. 11.

EXAMPLES

The individual layers were prepared as follows:

(a) Topsheet 3

Used was through-air bonded nonwoven fabric having a basis weight of 25 g/m$^2$, comprising sheath/core bicomponent synthetic fibers (fineness of 2.2 dtex; fiber length of 44 mm), of which the core component was polyethylene terephthalate containing titanium oxide in an amount of 1.1% of the fiber weight and the sheath component was polyethylene. In the following measurement, the topsheet 3 had a width of 130 mm, a length of 200 mm, and a weight of 0.637 g.

(b) Liquid Permeable Layer 5

Used was through-air bonded nonwoven fabric (basis weight of 25 g/m$^2$; mean thickness of 1.75 mm; mean density of 0.0175 g/cm$^3$) comprising eccentric sheath/core bicomponent synthetic fibers (fineness of 4.4 dtex; fiber length of 50 mm), of which the core component was polypropylene and the sheath component was polyethylene. This fabric was folded in three for use. In the following measurement, the liquid permeable layer 5 had a width of 100 mm, a length of 200 mm, and a weight of 0.415 g.

(c) Liquid Passage Holes 25

After the topsheet 3 was laid on the liquid permeable layer 5, the liquid passage holes 25 passing through both the topsheet 3 and the liquid permeable layer 5 were formed with a roll having pins heated to 100 degrees centigrade and a roll having holes for receiving the pins and heated to 70 degrees centigrade. The liquid passage holes 25 had an opening diameter of 2 mm and were arranged at a pitch of 5.5 mm in the Y-direction and at a pitch of 3.5 mm in the X-direction.

(d) Liquid Acquisition Layer 6

Used was air-laid nonwoven fabric (air-laid pulp) having a basis weight of 40 g/m², comprising: 60% by weight of chemical pulp; 26% by weight of sheath/core bicomponent synthetic fibers (fineness of 1.7 dtex; fiber length of 13 mm), of which the core component was polyethylene terephthalate and the sheath component was polyethylene; and 14% by weight of ethylene-vinyl acetate copolymer emulsion adhesive. This fabric was folded in two for use as the absorbent sheet 8. In the following measurement, the liquid acquisition layer 6 had a width of 50 mm, a length of 100 mm, and a weight of 0.205 g.

For Comparative Example 1 in Table 1, the absorbent sheet 8 was used as the liquid acquisition layer 6 without three-dimensional deformation. When measured five times in a dry state, the absorbent sheet 8 had a thickness of 0.928 mm on average.

Before three-dimensional deformation, the absorbent sheet 8 had a mean density of 0.075 g/cm³. When measured after the liquid acquisition layer 6 was three-dimensionally shaped, the dry tensile breaking strength in the Y-direction was 3.46 N/25 mm, while the dry tensile breaking strength in the X-direction was 2.83 N/25 mm.

The liquid acquisition layer 6 was obtained by three-dimensionally shaping the absorbent sheet 8. The longitudinal ribs 6a had a width of 3 mm at a height of h1/2, the transverse ribs 6b had a width of 2.5 mm at a height of h2/2, and the recesses 6c had an opening area of 15 mm² at a height of h2/2.

However, the clearance between the upper mold 40 and the lower mold 50 was varied for Comparative Example 2 and Examples 1 to 8 shown in Table 1 so as to change the thickness (h1 in FIG. 6) of the liquid acquisition layer 6 in a dry state.

In Comparative Example 2, since the thickness was 1.192 mm, the space volume of the recess 6c was calculated as follow: {15×(1.192−0.928)}=3.96 mm³. As calculated in the same manner, the space volume was 8.61 mm³ in Example 2 of the smallest thickness among Examples 1–8, while the space volume was 32.64 mm³ in Example 8 of the largest thickness. Therefore, the space volume of the recess was varied from 8.61 to 32.64 mm³ in Examples 1–8.

(e) Liquid Absorbent Layer 4

The liquid absorbent layer 4 was prepared such that 8 g of chemical pulp and 0.15 g of absorbent polymer were evenly mixed, accumulated into a body having a width of 70 mm, a length of 200 mm, and a density of 0.069 g/cm³, and then wrapped in tissue paper of 15 g/m².

(1) Measurement of Thickness

Measurements of thickness using UF-60A manufactured by Daiei Kagaku Seiki Co., Ltd. were made in a dry state and after application of pressure in state a wet state.

(2) Drip Test

The individual liquid acquisition layers 6 prepared for Comparative Examples 1–2 and Examples 1–8 shown in Table 1 were fixed to an opening of a 50 ml beaker. Artificial menstrual blood was allowed to fall on the center of the liquid acquisition layer 6 from a level 5 mm high continuously at a flow rate of 3 ml/min by using an auto burette. The time required for the first drip of artificial menstrual blood to fall into the beaker was measured since the fall was started (in terms of seconds).

As used herein, the artificial menstrual blood was prepared such that a solution was obtained by adding 300 g of glycerin, 30 g of carboxymethylcellulose sodium and 40 g of sodium chloride to 4 liter of ion-exchanged water, followed by stirring, and the solution was colored with food red.

(3) Absorption Test Under Load

Figure 12A:
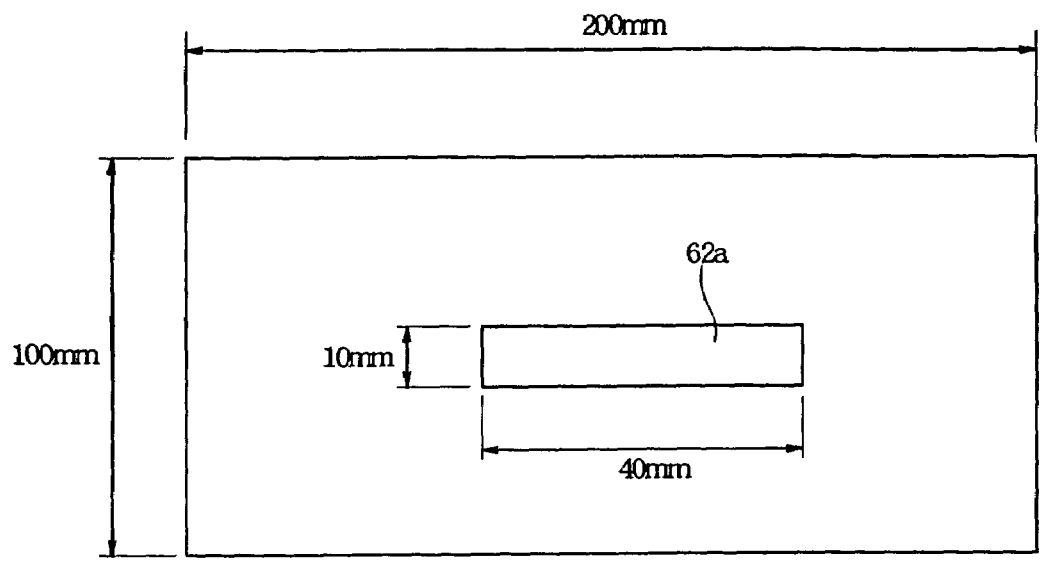
FIG. 12A is a plan view showing an acrylic plate used for absorption test under load.
Figure 12B:
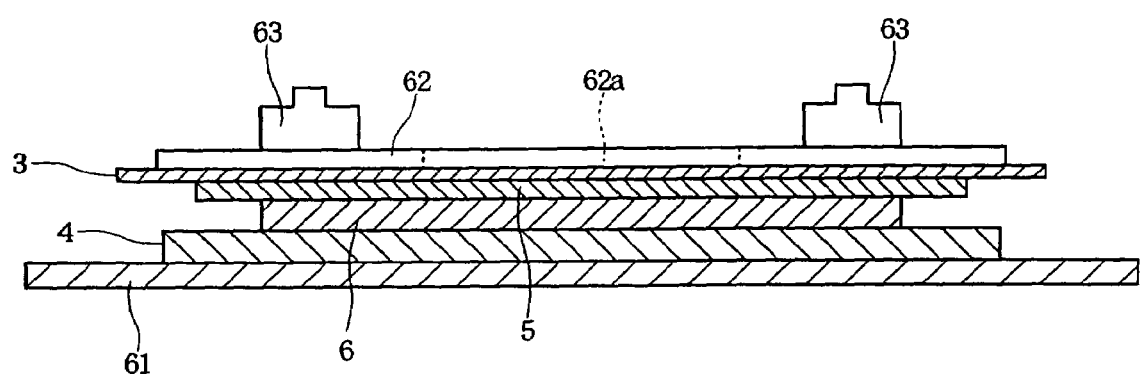
FIG. 12B is a sectional view for explanation of the absorption test under load.

As shown in FIG. 12B, the liquid absorbent layer 4, the liquid acquisition layer 6 and the topsheet 3 integrated with the liquid permeable layer 5 were stacked on a flat test board 61 in the order named above. An acrylic plate 62 dimensioned as shown in FIG. 12A was laid on the stack with its opening 62a coinciding with the center of the stack. Then, 900 g of weights 63 and 63 were placed in front of and behind the opening 62a. The weight of the acrylic plate itself was 115 g.

The artificial menstrual blood was applied to the opening 62a at a flow rate of 95 ml/min by using an auto burette. 3 ml of artificial menstrual blood was first applied, and the time (seconds) required for the liquid to disappear from the surface of the topsheet 3 in the opening 62a was measured since the beginning of the liquid application. 30 seconds after disappearance of the firstly applied liquid from the surface of the topsheet 3, 4 ml of artificial menstrual blood was applied, and the permeation time was measured in the same manner. 5 minutes after disappearance of the secondly applied liquid from the surface of the topsheet 3, 3 ml of artificial menstrual blood was applied, and the permeation time was measured in the same manner.

1 minute after disappearance of the finally applied liquid from the surface of the topsheet 3, the acrylic plate 62 and the weights 63 and 63 were removed and the thickness of the liquid acquisition layer 6 was measured. The thickness change (in terms of percentage) was calculated as follow: (thickness after absorption test under load/thickness after shaping in a dry state)×100.

The results of measurements are shown in Table 1.

TABLE 1

|  | Com. Ex. 1 | Com. Ex. 2 | Ex. 1 | Ex. 2 | Ex. 3 | Ex. 4 | Ex. 5 | Ex. 6 | Ex. 7 | Ex. 8 |
| --- | --- | --- | --- | --- | --- | --- | --- | --- | --- | --- |
| Temperature (Upper and Lower Molds) | Not Processed | 80 | 120 | 80 | 80 | 80 | 60 | 80 | 100 | 80 |
| Thickness after Shaping (Dry) on Average (n = 5) | 0.928 | 1.192 | 2.548 | 1.502 | 1.678 | 2.018 | 2.454 | 2.404 | 2.580 | 3.104 |

TABLE 1-continued

|  |  | Com. Ex. 1 | Com. Ex. 2 | Ex. 1 | Ex. 2 | Ex. 3 | Ex. 4 | Ex. 5 | Ex. 6 | Ex. 7 | Ex. 8 |
| --- | --- | --- | --- | --- | --- | --- | --- | --- | --- | --- | --- |
| Drip Test | (Sec.) | 33.0 | 16.7 | 13.0 | 14.0 | 11.7 | 13.3 | 14.0 | 16.7 | 15.0 | 19.0 |
| Absorption Test under Load | 3 ml | 5.57 | 6.59 | 4.43 | 6.07 | 5.22 | 4.49 | 4.64 | 4.43 | 4.40 | 4.27 |
| Left for 5 Minutes | 4 ml | 12.37 | 13.36 | 6.82 | 10.45 | 10.17 | 9.34 | 10.12 | 8.14 | 8.63 | 8.69 |
|  | 3 ml | 15.69 | 15.52 | 7.04 | 11.21 | 12.59 | 11.86 | 12.24 | 10.21 | 9.65 | 9.28 |
| Total Time | (Sec.) | 33.63 | 35.48 | 18.29 | 27.72 | 27.98 | 25.69 | 27.00 | 22.78 | 22.68 | 22.24 |
| Thickness of Acquisition Layer after Absorption Test under Load |  | 0.80 | 0.85 | 2.15 | 1.20 | 1.35 | 1.47 | 1.38 | 1.58 | 1.60 | 1.54 |
| Thickness Change (%) |  | 86.21 | 71.31 | 84.38 | 79.89 | 80.45 | 72.84 | 56.23 | 65.72 | 62.02 | 49.61 |

It can be seen from Table 1 that Examples 1–8 are all excellent in both dripping property and liquid permeability determined by the absorption test under load.

Although the liquid permeable layer 5 is disposed between the topsheet 3 and the liquid acquisition layer 6 in the foregoing embodiments, the liquid acquisition layer 6 may be in direct contact with the topsheet 3 without providing the liquid permeable layer 5.

According to the present invention, as has been described hereinabove, liquid applied in a large amount at a time can be rapidly absorbed by the liquid absorbent layer after retention beneath the topsheet, preventing the liquid from remaining in the topsheet.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but to include all possible embodiments which can be embodied within a scope encompassed and equivalent thereof with respect to the feature set out in the appended claims.

What is claimed is:

1. An absorbent article comprising: a liquid-permeable topsheet appearing on a skin surface; a backsheet appearing on a garment surface; and a liquid absorbent layer disposed between the topsheet and the backsheet, wherein a liquid acquisition layer is disposed between the liquid absorbent layer and the topsheet, the liquid acquisition layer being kept in a three-dimensionally deformed state, wherein the liquid acquisition layer is an absorbent sheet that is three-dimensionally deformed to include: longitudinal ribs projecting toward the topsheet and extending parallel with each other in a longitudinal direction of the article; and transverse ribs projecting toward the topsheet and extending in a transverse direction of the article, the transverse ribs being arranged at intervals in the longitudinal direction and connecting adjacent longitudinal ribs, thereby providing a plurality of recesses surrounded by the longitudinal ribs and the transverse ribs, wherein at least the longitudinal ribs are in contact with the topsheet, whereas bottoms of the recesses are in contact with the liquid absorbent layer wherein the liquid acquisition layer has flat portions extending from each of two opposing sides of an uneven portion that is defined by the longitudinal and transverse ribs, each flat portion having a greater width and a lower fiber density than any of the longitudinal ribs.

2. An absorbent article as set forth in claim 1, wherein a height from the bottoms of the recesses to tops of the transverse ribs is smaller than a height from the bottoms of the recesses to tops of the longitudinal ribs.

3. An absorbent article as set forth in claim 1, wherein the individual recesses are elongated to be longer in the longitudinal direction than in the transverse direction.

4. An absorbent article as set forth in claim 1, wherein each recess has a space volume of 8 to 80 $mm^3$.

5. An absorbent article as set forth in claim 1, wherein the liquid acquisition layer has low-density portions where fiber-to-fiber distance is increased by concentration of tensile stress when the absorbent sheet is three-dimensionally deformed.

6. An absorbent article as set forth in claim 1, wherein the liquid acquisition layer is a stack of two or more absorbent sheets that are three-dimensionally deformed together.

7. An absorbent article as set forth in claim 1, wherein when measured in the longitudinal direction, the liquid acquisition layer has a dry tensile breaking strength of at least 2.5 N/25 mm width.

* * * * *